United States Patent
Raths et al.

(10) Patent No.: US 6,277,359 B1
(45) Date of Patent: Aug. 21, 2001

(54) DEODORIZING FORMULATION

(75) Inventors: Hans-Christian Raths, Monheim (DE); Manfred Biermann, Cincinnati, OH (US); Karl-Heinz Maurer, Erkrath (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/493,723

(22) Filed: Jan. 28, 2000

Related U.S. Application Data

(60) Provisional application No. 60/117,930, filed on Jan. 29, 1999.

(51) Int. Cl.$^7$ ............................... A61K 7/32; A61K 7/38; A61K 7/00
(52) U.S. Cl. ............................... 424/65; 424/68; 424/401
(58) Field of Search ............................... 424/65, 68, 76.1

(56) References Cited

U.S. PATENT DOCUMENTS

| | | | |
|---|---|---|---|
| 4,172,887 | 10/1979 | Vanlerberghe et al. | 424/70 |
| 5,705,169 | 1/1998 | Stein et al. | 424/401 |
| 5,730,960 | 3/1998 | Stein et al. | 424/59 |
| 5,922,670 | * 7/1999 | Knuebel et al. | 510/426 |
| 5,968,488 | * 10/1999 | Wachter et al. | 424/65 |

FOREIGN PATENT DOCUMENTS

| | | |
|---|---|---|
| 1165574 | 3/1964 | (DE) . |
| 2024051 | 5/1986 | (DE) . |
| 19503061 | 8/1996 | (DE) . |
| 693471 | 1/1996 | (EP) . |
| 694521 | 1/1996 | (EP) . |
| 818450 | 1/1998 | (EP) . |
| 2252840 | 8/1975 | (FR) . |

OTHER PUBLICATIONS

Umbach (Ed.), "Kosmetik", Thieme Verlag, Stuttgart, 1988, pp. 141 et seq.
A. Hinze, Fette & Öle, 26, (1994), pp. 47–51.
Tronnier, et al., J. Soc. Cosmetic Chemists, 24, (1973), pp. 281–290.
Graham, et al., J. Pharm. Pharmacol., 26, (1974) pp. 531–534.
Todd, et al., Cosm. Toil., 91, (Jan., 1976), pp. 29–32.
Lochhead, et al., Cosm. Toil., 108, (May, 1993), pp. 95–135.
Finkel, SÖFW–Journal, 122, (1996), pp. 543–548.
"Kosmetische Fäbemittel", Farbstoffkommission der Deutschen Forschungsgemeinschaft, Verlag Chemie, Weinhein, (1984), pp. 81–106.

* cited by examiner

*Primary Examiner*—Shelley A. Dodson
*Assistant Examiner*—Konata M. George
(74) *Attorney, Agent, or Firm*—John E. Drach; Steven J. Trzaska

(57) ABSTRACT

A composition containing: (a) a gemini surfactant selected from the group consisting of a dimer alcohol-bis-sulfate, a dimer alcohol-bis-ether sulfate, a trimer alcohol-tris-sulfate, a trimer alcohol-tris-ether sulfate, and mixtures thereof; (b) aluminum chlorohydrate; and (c) a component selected from the group consisting of an esterase inhibitor, a bactericidal agent, a bacteriostatic agent, and mixtures thereof.

14 Claims, No Drawings

DEODORIZING FORMULATION

CROSS-REFERENCE TO RELATED APPLICATIONS

This application claims priority from U.S. provisional application Ser. No. 60/117,930, filed Jan. 29, 1999, the disclosure of which is incorporated herein by reference.

BACKGROUND OF THE INVENTION

This invention relates to deodorizing formulations containing dimer alcohol-bis- and trimer alcohol-tris-sulfates and -ether sulfates, aluminium chlorohydrate, esterase inhibitors and/or bactericidal or bacteriostatic agents and to the use of dimer alcohol-bis- and trimer alcohol-tris-sulfates and -ether sulfates for the production of cosmetic formulations, for example deodorizing formulations.

In the field of personal hygiene, deodorants are used to eliminate troublesome body odors. Body odors are formed by the bacterial decomposition of basically odorless perspiration, particularly in the damp underarm regions or under similar conditions favorable to microorganism growth. Body odors can be masked by suitable perfumes. They can also be controlled by using formulations which inhibit the actual secretion of perspiration or its decomposition (so-called antihydrotics, antiperspirants or antitranspirants). Typical examples of such substances are aluminium compounds, such as aluminium sulfate or aluminium chlorohydrate, zinc salts and citric acid compounds. An overview of these agents was published, for example, in Umbach (Ed.), "Kosmetik", pages 141 et seq., Thieme Veriag, Stuttgart, 1988.

However, it is clear from everyday living that the problem of odor inhibition, particularly in heat or in the event of bodily activity, has by no means been completely solved. Commercial products are unable permanently to suppress the secretion of perspiration or the formation of odors. Instead, their inhibiting effect is of limited duration and is also dependent on the extent to which perspiration is secreted. Accordingly, there is a constant need for improved products which minimize the secretion of perspiration and reduce the formation of body odors and which, at the same time, show increased dermatological compatibility, i.e. reduced irritation potential towards particularly sensitive skin. The problem addressed by the present invention was to provide such products.

DESCRIPTION OF THE INVENTION

The present invention relates to deodorizing formulations containing
(a) dimer alcohol-bis- and trimer alcohol-tris-sulfates and/or -ether sulfates,
(b) aluminium chlorohydrate,
(c) esterase inhibitors and/or
(d) bactericidal or bacteriostatic agents.

The present invention also relates to the use of dimer alcohol-bis- and trimer alcohol-tris-sulfates and/or -ether sulfates for the production of cosmetic formulations such as, for example, deodorizing formulations.

The use of aluminium chlorohydrates, esterase inhibitors (for example triethyl citrate) and bactericidal agents (for example chitosan) for the production of deodorizing and/or perspiration-inhibiting compositions is known from the prior art. It has surprisingly been found that dimer alcohol-bis- and trimer alcohol-tris-sulfates and/or -ether sulfates inhibit the activity of esterolytic enzymes, even in the lower ppm range, and that a synergistic deodorizing effect is obtained together with the components mentioned above. These surfactants act selectively on serine esterases and serine proteases without impairing the biological equilibrium of the skin flora. At the same time, the use of dimer alcohol-bis- and trimer alcohol-tris-sulfates and/or -ether sulfates leads to an improvement in the skin-cosmetic compatibility of the products so that they may also be used in cosmetic formulations.

Dimer Alcohol-bis- and Trimer Alcohol-tris-sulfates and/or -ether Sulfates

The dimer alcohol-bis- and trimer alcohol-tris-sulfates and/or -ether sulfates according to the invention, which form component (a), are so-called gemini surfactants. They are distinguished by two anionic sulfate groups which are generally arranged at a distance of about 18 carbon atoms which guarantees that the two hydrophilic groups are able to act independently of one another.

These surfactants are produced in known manner (cf. DE 19503061 A1) by sulfation of dimer and/or trimer alcohols or addition products thereof with alkylene oxides at 25 to 70° C. and subsequent neutralization with a base (pH range 6.5 to 8.5). After neutralization, the sulfation products can be bleached in known manner by addition of hydrogen peroxide or sodium hypochlorite.

The dimer and trimer alcohols are commercially available compounds and may be obtained, for example, from dimer and trimer fatty acids which are generally mixtures of acyclic and cyclic dicarboxylic acids containing on average 36 to 44 carbon atoms [cf. A. Hinze, Fette & Öle, 26, (1994)]. The corresponding alkoxylates, for example the ethoxylates and/or propoxylates, may be obtained in known manner by alkoxylation of the dimer and trimer alcohols with a degree of ethoxylation of 1 to 20 and preferably 2 to 10. Suitable sulfonating agents are, for example, sulfuric acid, oleum, chlorosulfonic acid, aminosulfonic acid and gaseous sulfur trioxide. The neutralization step is carried out with bases, such as alkali metal hydroxides, alkaline earth metal oxides and hydroxides, ammonia, alkanolamines and Aluminium Chlorohydrate The aluminium chlorohydrates of component (b) are colorless hygroscopic crystals which readily coalesce in air and which accumulate during the concentration of aqueous aluminium chloride solutions by evaporation. Aluminium chlorohydrate is used for the production of antiperspirant and deodorizing formulations and probably acts by contracting or blocking the sweat glands by protein precipitation and/or removal of moisture [cf. J. Soc. Cosm. Chem. 24, 281 (1973)]. An aluminium chlorohydrate which corresponds to the formula $[Al_2(OH)_5Cl].2.5H_2O$ is commercially available under the name of Locron® from Hoechst AG of Frankfurt, FRG. This aluminium chlorohydrate is particularly preferred for the purposes of the invention [cf. J. Pharm. Pharmacol. 26 531 (1975)].

Esterase Inhibitors

When perspiration is present in and around the underarm region, extracellular enzymes—esterases, preferably proteases and/or lipases—which cleave esters and thus emit odor-forming substances are activated by bacteria. The esterase inhibitors of component (c), preferably trialkyl citrates, such as trimethyl citrate, tripropyl citrate, tributyl citrate and, in particular, triethyl citrate (Hydagen® CAT, Henkel KGaA, Düsseldorf, FRG), inhibit the enzyme activity and thus reduce odor formation. The free acid is probably released by the cleavage of the citric acid ester, reducing the pH value on the skin to such an extent that the enzymes are inactivated by acylation. Other substances suitable for use as esterase inhibitors are dicarboxylic acids and esters thereof such as, for example, glutaric acid, glutaric acid monoethyl ester, glutaric acid diethyl ester, adipic acid, adipic monoethyl ester, adipic acid diethyl ester, malonic acid and malonic acid diethyl ester, hydroxycarboxylic acids and esters thereof such as, for example, citric acid, malic acid, tartaric acid or tartaric acid diethyl ester.

Bactericides or Bacteriostatic Agents

Bactericides or bacteriostatic agents (component (d)), which influence the germ flora and kill off or inhibit the growth of perspiration-decomposing bacteria, may also be present in the formulations. Typical examples are, in particular, chitosan and phenoxyethanol. 5-Chloro-2-(2,4-dichlorophenoxy)-phenol, which is marketed by Ciba-Geigy of Basel, Switzerland under the name of Irgasan®, has also proved to be particularly effective.

COMMERCIAL APPLICATIONS

Dimer alcohol-bis-and trimer alcohol-tris-sulfates and ether sulfates have proved to be enzyme-inhibiting for the described application. Accordingly, the present invention relates to their use for the production of cosmetic formulations such as, for example, hair shampoos, hair lotions, foam baths, creams, gels or lotions.

They may be used in particular for the production of deodorizing formulations either on their own or together with other deodorizing agents, such as aluminium chlorohydrates, other esterase inhibitors and/or bactericidal or bacteriostatic agents.

In one preferred embodiment of the invention, components (a) to (d) may advantageously be used in the following quantities, based on the solids content:
(a) 0.01 to 50, preferably 0.1 to 10% by weight of dimer alcohol-bis-and trimer alcohol-tris-sulfates and -ether sulfates,
(b) 1.0 to 50, preferably 10 to 40% by weight of aluminium chlorohydrate,
(c) 0.01 to 20, preferably 1.0 to 5.0% by weight of esterase inhibitors and/or
(d) 0.01 to 5.0, preferably 0.1 to 1.0% by weight of bactericidal or bacteriostatic agents,
with the proviso that the quantities shown add up to 100% by weight. The figures apply to the active substance content of the components.

To enable the active substances to be applied to the skin in a measurable, economic, convenient and cosmetically attractive manner, they are normally incorporated in formulation bases. The most important of these include alcoholic and aqueous/alcoholic solutions, emulsions, gels, oils, wax/fat compounds, stick preparations and powders. Thus, the formulations according to the invention may contain, for example, up to 60% by weight of lower aliphatic alcohols, preferably ethanol, and organic acids, for example glycolic acid. Other ingredients include superfatting agents, emulsifiers, antioxidants, talcum, silica (for example as a support for the aluminium chlorohydrate), perfume oils, essential oils, dyes and—for spray applications—propellent gases such as, for example, propane and/or butane. The formulations are preferably marketed as rollers (roll-on emulsions), sticks, deodorant or pump sprays.

The cosmetic formulations may also contain germ inhibitors, mild surfactants, oils, pearlescing waxes, consistency promoters, thickeners, polymers, silicone compounds, fats, waxes, stabilizers, biogenic agents, antidandruff agents, film formers, swelling agents, UV protection factors, hydrotropes, preservatives, insect repellents, self-tanning agents, solubilizers and the like.

Other Auxiliaries and Additives

Typical examples of germ inhibitors are preservatives which act specifically against gram-positive bacteria such as, for example, 2,4,4'-trochloro-2'-hydroxydiphenyl ether, chlorhexidine (1,6-di-(4-chlorophenyl-biguanido)-hexane) or TCC (3,4,4'-trichlorocarbanilide). Numerous perfumes and essential oils also have antimicrobial properties. Typical examples are the active substances eugenol, menthol and thymol in nettle, mint and thyme oil. An interesting natural deodorant is the terpene alcohol farnesol (3,7,11-trimethyl-2,6,10-dodecatrien-1-ol) which is present in linden blossom oil and which smells of lily-of-the-valley. Glycerol monolaurate has also been successfully used as a bacteriostatic agent. The percentage content of the additional germ-inhibiting agents is normally about 0.1 to 2% by weight, based on the solids component of the formulations.

Typical examples of suitable mild, i.e. dermatologically compatible, surfactants, are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, ether carboxylic acids, alkyl oligoglucosides, fatty acid glucamides, alkyl amidobetaines and/or protein fatty acid condensates (preferably based on wheat proteins).

Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more particularly dioctyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons.

Suitable emulsifiers are, for example, nonionic surfactants from at least one of the following groups:
(1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;
(2) $C_{12/18}$ fatty acid monoesters and diesters of adducts of 1 to 30 moles of ethylene oxide with glycerol;
(3) glycerol monoesters and diesters and sorbitan monoesters and diesters of saturated and unsaturated fatty acids containing 6 to 22 carbon atoms and ethylene oxide adducts thereof;
(4) alkyl mono- and oligoglycosides containing 8 to 22 carbon atoms in the alkyl group and ethoxylated analogs thereof;
(5) adducts of 15 to 60 moles of ethylene oxide with castor oil and/or hydrogenated castor oil;

(6) polyol esters and, in particular, polyglycerol esters such as, for example, polyglycerol polyricinoleate, polyglycerol poly-12-hydroxy-stearate or polyglycerol dimerate. Mixtures of compounds from several of these classes are also suitable;

(7) adducts of 2 to 15 moles of ethylene oxide with castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) mono-, di- and trialkyl phosphates and mono-, di- and/or tri-PEG-alkyl phosphates and salts thereof;

(10) wool wax alcohols;

(11) polysiloxane/polyalkyl polyether copolymers and corresponding derivatives;

(12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol or polyglycerol;

(13) polyalkylene glycols and

(14) glycerol carbonate.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use are known from the prior art. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N, N-dimethyl ammonium glycinates, for example cocoacylaminopropyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO₃H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, preferably methyl-quarternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlescing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency promoters mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat®, (BASF), condensation products of polyglycols and amines, quaternized collagen polypeptides such as, for example, Lauryldimonium Hydroxypropyl Hydrolyzed Collagen (Lamequat® L, Grünau GmbH), quaternized wheat polypeptides, polyethyleneimine, cationic silicone polymers such as, for example, Amidomethicone, copolymers of adipic acid and dimethylaminohy droxypropyl diethylenetriamine (Cartaretine® Sandoz AG), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromo butane, with bis-dialkylamines, for example bis-dimethylamino-1,3-propane, cationic guar gum such as, for example, Jaguar® CBS, Jaguar®C-17, Jaguar®C-16 of Celanese, USA, quaternized ammonium salt polymers such as, for example, Mirapol®A-15, Mirapol®AD-1, Mirapol®AZ-1 of Miranol, USA.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. In addition, a detailed review of suitable liquid silicones was published by Todd et al. in Cosm. Toil. 91, 27 (1976).

Typical examples of fats are glycerides while suitable waxes are inter alia beeswax, carnauba wax, candelilla wax, montan wax, paraffin wax or microwaxes, optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts, and vitamin complexes.

Suitable antidandruff agents are climbazol, octopirox and zinc pyrethion. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Sun (UV) protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP-B1 0693471;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP-A1 0818450;

propane-1,3-diones such as, for example, 1-(4-tert.butylphenyl)-3-(4'-methoxyphenyl)-propane-1,3-dione;

ketotricyclo(5.2.1.0)decane derivatives as described in EP-B1 0694521.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione. The UV-A and UV-B filters may of course also be used in the form of mixtures. Besides the soluble substances mentioned, insoluble light-blocking pigments, i.e. finely dispersed metal oxides or salts, may also be used for this purpose. Examples of suitable metal oxides are, in particular, zinc oxide and titanium dioxide and oxides of iron, zirconium, silicon, manganese, aluminium and cerium and mixtures thereof. Suitable salts are silicates (talcum), barium sulfate or zinc stearate. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. So-called micro- or nanopigments are preferably used in sun protection products. Micronized zinc oxide is preferably used.

Other suitable UV filters can be found in P. Finkel's review in SÖFW-Journal 122, 543 (1996).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to pmole/kg) also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethtylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, lso-E-Super, Fixolide NP, evernyl, iraldein gamma, phenylacetic acid, geranyl acetate, benzyl acetate, rose oxide, romillate, irotyl and floramate.

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

EXAMPLES

The effectiveness of the formulations according to the invention was representatively determined through their inhibition of esterase. To this end, the residual activity of the test mixtures after acting on esterase for 15 minutes in concentrations of 0.1 to 5,000 ppm at pH 6 (adjusted with NaOH) was determined parallel to a non-inhibited control (standard=100%). Compositions 1 and 2 correspond to the invention, compositions C1 to C4 are intended for comparison. The Examples are summarized in Table 1 (quantities in % by weight).

TABLE 1

Formulations and esterase inhibition

| Components | 1 | 2 | C1 | C2 | C3 | C4 |
|---|---|---|---|---|---|---|
| $C_{36}$ Dimer diol disulfate sodium salt | 4 | — | — | — | — | — |
| Dimer diol + 30 EO | — | — | 4 | — | — | — |
| Dimer diol + 20 EO disulfate sodium salt | — | 4 | — | — | — | — |
| Aluminum chlorohydrate | — | — | — | 50 | — | 50 |
| Triethyl citrate | — | — | — | — | 5 | 5 |
| Ethanol | — | 20 | 20 | 20 | 20 | 20 |
| Water | | | | to 100 | | |
| Esterase activity at | | | | | | |
| 5000 ppm [%] | — | 6 | 12 | — | — | — |
| 2000 ppm [%] | — | 24 | 30 | 100 | 77 | 75 |
| 500 ppm [%] | — | 26 | 42 | — | — | — |
| 100 ppm [%] | 0 | 46 | 59 | — | — | — |
| 10 ppm [%] | 0 | — | — | — | — | — |
| 1 ppm [%] | 5 | — | — | — | — | — |
| 0.1 ppm [%] | 72 | — | — | — | — | — |

What is claimed is:

1. A composition comprising:
   (a) a gemini surfactant selected from the group consisting of a dimer alcohol-bis-sulfate, a dimer alcohol-bis-ether sulfate, a trimer alcohol-tris-sulfate, a trimer alcohol-tris-ether sulfate, and mixtures thereof;
   (b) aluminum chlorohydrate; and
   (c) a component selected from the group consisting of an esterase inhibitor, a bactericidal agent, a bacteriostatic agent, and mixtures thereof.

2. The composition of claim 1 wherein the esterase inhibitor is a trialkyl citrate.

3. The composition of claim 1 wherein the gemini surfactant is present in the composition in an amount of from 0.01 to 50% by weight, based on the solids content of the composition.

4. The composition of claim 1 wherein the aluminum chlorohydrate is present in the composition in an amount of from 1.0 to 50% by weight, based on the solids content of the composition.

5. The composition of claim 1 wherein component (c) is an esterase inhibitor, and is present in the composition in an amount of from 0.01 to 20% by weight, based on the solids content of the composition.

6. The composition of claim 5 further containing from 0.01 to 5.0% by weight, based on the solids of the composition, of a bactericidal or bacteriostatic agent.

7. A process for inhibiting body odor comprising contacting human skin with a composition containing:
   (a) a gemini surfactant selected from the group consisting of a dimer alcohol-bis-sulfate, a dimer alcohol-bis-ether sulfate, a trimer alcohol-tris-sulfate, a trimer alcohol-tris-ether sulfate, and mixtures thereof;
   (b) aluminum chlorohydrate; and
   (c) a component selected from the group consisting of an esterase inhibitor, a bactericidal agent, a bacteriostatic agent, and mixtures thereof.

8. The process of claim 7 wherein the esterase inhibitor is a trialkyl citrate.

9. The process of claim 7 wherein the gemini surfactant is present in the composition in an amount of from 0.01 to 50% by weight, based on the solids content of the composition.

10. The process of claim 7 wherein the aluminum chlorohydrate is present in the composition in an amount of from 1.0 to 50% by weight, based on the solids content of the composition.

11. The process of claim 7 wherein component (c) is an esterase inhibitor, and is present in the composition in an amount of from 0.01 to 20% by weight, based on the solids content of the composition.

12. The process of claim 11 wherein the composition further contains from 0.01 to 5.0% by weight, based on the solids of the composition, of a bactericidal or bacteriostatic agent.

13. A personal skin care composition containing a gemini surfactant selected from the group consisting of a dimer alcohol-bis-sulfate, a dimer alcohol-bis-ether sulfate, a trimer alcohol-tris-sulfate, a trimer alcohol-tris-ether sulfate, and mixtures thereof.

14. The composition of claim 13 wherein the gemini surfactant is present in the composition in an amount of from 0.01 to 50% by weight, based on the solids content of the composition.

* * * * *